United States Patent [19]

Smith

[11] 3,953,438

[45] *Apr. 27, 1976

[54] PROCESS FOR THE PREPARATION OF LACTAMS

[75] Inventor: Joseph A. Smith, Richmond, Va.

[73] Assignee: Allied Chemical Corporation, New York, N.Y. 10020

[*] Notice: The portion of the term of this patent subsequent to Oct. 21, 1992, has been disclaimed.

[22] Filed: Feb. 7, 1975

[21] Appl. No.: 548,064

[52] U.S. Cl. .......... 260/239.3 A; 260/293.86 .........
[51] Int. Cl.$^2$ ............... C07D 201/04 .....................
[58] Field of Search ............ 260/239.3A, 293.86...

[56] References Cited

UNITED STATES PATENTS

| | | | |
|---|---|---|---|
| 2,221,369 | 11/1940 | Cass | 260/239.3A |
| 3,914,217 | 10/1975 | Smith | 260/239.3A |

Primary Examiner—Henry R. Jiles
Assistant Examiner—Robert T. Bond
Attorney, Agent, or Firm—Fred L. Kelly

[57] ABSTRACT

This invention relates to a process for the production of lactams by catalytic rearrangement of cycloketoximes in the presence of oleum. More specifically the invention relates to improving yields of lactam while reducing undesirable by-product formation by use of two stages of rearrangement with correlated adjustment of reaction conditions in each stage. Critical variables in each stage include acid concentration, free $SO_3$ concentration, percent oxime added, reaction temperature and extent of mixing. Normally, the oxime fed to the process contains up to 6 percent water.

9 Claims, No Drawings

3,953,438

PROCESS FOR THE PREPARATION OF LACTAMS

BACKGROUND OF THE INVENTION

This invention relates to a process for the production of lactams by catalytic rearrangement of ketoximes. It relates in particular to a process for the production of lactams by catalytic rearrangement of cycloketoximes in the presence of oleum.

It is known that cyclic ketoximes, especially cyclohexanone oxime, can be rearranged into the corresponding lactams by the action of acid reagents such as oleum, concentrated sulfuric acid or acetic anhydride.

It is also known that the rearrangement of cyclic ketoximes can be carried out at elevated temperatures of 200° to 450° C. in the gaseous phase in the presence of solid catalysts. Strongly acid catalysts are used such as various phosphoric acids, alkali metal bisulfates or boric acid, in most cases applied to carriers.

U.S. Pat. No. 3,350,393, issued Oct. 31, 1967, involves converting cyclohexanone oxime into caprolactam by contacting the oxime with a solid catalyst at 210° to 450° C. and condensing caprolactam from the effluent reaction gas. The process includes the steps of quenching the reaction gas with liquid caprolactam having a temperature at least 10° C below the temperature of the gas mixture leaving the reaction zone and condensing caprolactam therefrom in a condensation zone by direct cooling with a low boiling solvent, e.g., water.

U.S. Pat. No. 3,418,314, issued Dec. 24, 1968, discloses an improved process for the production of lactams by molecular rearrangement of a cycloalkanone oxime in gaseous phase in the presence of a solid aluminum-containing catalyst.

U.S. Pat. No. 3,437,655, issued Apr. 8, 1969, is based on the discovery that cycloaliphatic ketoximes can be made to yield the corresponding lactams if the oxime is reacted as oxime hydrochloride with hydrogen chloride.

U.S. Pat. No. 3,503,958, issued Mar. 31, 1970, relates to the molecular rearrangement of oximes to lactams in the presence of an alumino-silicate catalyst.

More recently, U.S. Pat. No. 3,553,204, issued Jan. 5, 1971, involves the continuous production of lactams from cyclic ketoximes using mineral acids as a catalyst and cycling oxime and acid by way of nozzles from continuous mixers in lieu of using agitator vessels.

SUMMARY OF THE INVENTION

This invention relates to an improved process for the production of lactams by catalytic rearrangement of cycloketoximes, for example, cyclohexanone oxime, in the presence of oleum. By this process, the yield of lactam is improved and production of undesirable by-products is reduced. Moreover, oleum requirements are significantly reduced as compared with prior art processes.

The process of the present invention may be summarized as follows. A process for the production of lactams by catalytic rearrangement of cycloketoximes in the presence of oleum comprising:

(a) Continuously feeding a first portion of a cycloketoxime consisting of 65 to 85 parts by weight of cycloketoxime having a water content of up to 6 weight percent to a first catalytic rearrangement zone containing a circulating reaction mass having a sulfuric acid to lactam weight ratio of 1.37 to 1.80, a free $SO_3$ content of 2.4 to 14.0 weight percent, and a temperature of 50° to 105° C., said reaction mass being circulated at a rate at least 20 times the rate of feeding said cycloketoxime to said first catalytic rearrangement zone;

(b) Continuously feeding oleum to said first catalytic reaction zone in amount sufficient to maintain a sulfuric acid to lactam weight ratio of 1.37 to 1.80 in said zone, said oleum containing $SO_3$ in amount sufficient to react with all of the water in the cycloketoxime and maintain the free $SO_3$ content of the circulating reaction mass at 2.4 to 14.0 weight percent;

(c) Continuously feeding a portion of the circulating reaction mass from the first catalytic rearrangement zone substantially equivalent to the feed of cycloketoxime to said zone, to a second catalytic rearrangement zone containing a circulating reaction mass having a sulfuric acid to lactam weight ratio of at least 1.14, preferably 1.14 to 1.31, a free $SO_3$ content of at least 0.82, preferably 0.82 to 6.5 weight percent, and a temperature of 70° to 100° C., said reaction mass in said second catalytic rearrangement zone being circulated at a rate of at least 20 times the rate of feeding to said second catalytic rearrangement zone said portion of the circulating reaction mass from said first catalytic rearrangement zone;

(d) Continuously feeding a second portion of the cycloketoxime consisting of 15 to 35 parts by weight of the cycloketoxime having a water content oi up to 6 weight percent to said second catalytic rearrangement zone;

(e) Continuously withdrawing a portion of the circulating reaction mass from the second catalytic rearrangement zone substantially equivalent to the feed to said zone; and (f) Recovering lactam from the portion of the circulating reaction mass withdrawn from the second catalytic rearrangement zone.

For determination of the sulfuric acid to lactam weight ratio in said two catalytic rearrangement zones, the $SO_3$ present is considered equivalent to sulfuric acid, i.e., it is included in the calculation as fulfuric acid.

The residence time of the oxime in contact with the catalyst should amount to at least 3.0 to 10 seconds. A study of the reaction kinetics led to a decrease of reaction temperature from the normal prior art temperature of about 110° C. to preferably 70° to 100° C. This lower temperature produces crude lactam of excellent color.

The process according to the invention is suitable for rearranging cycloalkanone oximes which have 5 to 12 carbon atoms in the ring to the corresponding lactams. For example, cyclopentanone oxime, cyclohexanone oxime and methyl cyclohexanone oxime may be used. When higher homologs of cyclohexanone oxime are converted, solvent might have to be used.

DESCRIPTION OF THE PREFERRED EMBODIMENT

Although the Beckman rearrangement according to the invention is independent of the oxime used, the preferred embodiment is described in terms of the conversion of cyclohexanone oxime to ε-caprolactam. The preferred process is summarized as follows:

A process for the production of caprolactam by catalytic rearrangement of cyclohexanone oxime in the presence of oleum comprising:

(a) Continuously feeding a first portion of cyclohexanone oxime consisting of 65 to 85 parts by weight of cyclohexanone oxime having a water content of 0.1 to 5 weight percent to a first catalytic rearrangement zone containing a circulating reaction mass having a sulfuric acid to caprolactam weight ratio of 1.40 to 1.75, a free $SO_3$ content of 3.0 to 10.0 weight percent, and a temperature of 70° to 105° C., said reaction mass being circulated at a rate of 30 to 50 times the rate of feeding said cyclohexanone oxime to said first catalytic rearrangement zone;

(b) Continuously feeding oleum to said first catalytic reaction zone in amount sufficient to maintain a sulfuric acid to caprolactam weight ratio of 1.40 to 1.75 in said zone, said oleum containing $SO_3$ in amount sufficient to react with all of the water in the cyclohexanone oxime and maintain the free $SO_3$ content of the circulating reaction mass at 3.0 to 10.0 weight percent;

(c) Continuously feeding a portion of the circulating reaction mass from the first catalytic rearrangement zone substantially equivalent to the feed of cyclohexanone oxime to said zone, to a second catalytic rearrangement zone containing a circulating reaction mass having a sulfuric acid to caprolactam weight ration of 1.14 to 1.31, a free $SO_3$ content of 0.82 to 6.5 weight percent, and a temperature of 70° to 100° C., said reaction mass in said second catalytic rearrangement zone being circulated at a rate 30 to 50 times the rate of feeding to said second catalytic rearrangement zone said portion of the circulating reaction mass from said first catalytic rearrangement zone;

(d) Continuously feeding a second portion of the cyclohexanone oxime consisting of 15 to 35 parts by weight of the cyclohexanone oxime having a water content of 0.1 to 5 weight percent to said second catalytic rearrangement zone;

(e) Continuously withdrawing a portion of the circulating reaction mass from the second catalytic rearrangement zone substantially equivalent to the feed to said zone; and (f) Recovering caprolactam from the portion of the circulating reaction mass withdrawn from the second catalytic rearrangement zone.

In accordance with said preferred process, the product acid/lactam ratio can be reduced to 1.14 to 1.31 with excellent product quality. This advantage results largely by knowledge of the effect of free $SO_3$ in the two stages of rearrangement. It is desirable that all of the oleum be added in the first stage of rearrangement, whereas the oxime must be added in predetermined amounts to each of the two stages. Results further indicate the need for using oleum having relatively high oleum strength together with vigorous circulation in each of the two stages of rearrangement. Other factors of importance are outlined hereinafter.

In the first reaction stage, the $SO_3$ content of the oleum used is preferably above about 22–25 weight percent $SO_3$ when the water content of the oxime is relatively high, e.g., 5 weight percent water in the oxime. At any given acid/lactam ratio in the first stage of rearrangement, this will result in the presence of sufficient $SO_3$ to increase lactam production and decrease formation of impurities. It is desirable to provide sufficient mixing intensity to destroy localized hot spots caused by high free $SO_3$ in order to obtain the lowest possible amount of impurities. The data indicate that optimum free $SO_3$ in the circulating reaction mass in the first stage of rearrangement is in the range 3.5 to 6.5 weight percent $SO_3$ when using a conventional in-line mixer.

The recovery of caprolactam from the portion of the circulating reaction mass withdrawn from the second catalytic rearrangement zone may be accomplished by known procedures. Typically, the crude caprolactam rearrangement mass consisting essentially of caprolactam and sulfuric acid is sent to a reactor system together with ammonia, water and a solvent such as toluene. The sulfuric acid is neutralized and the caprolactam is simultaneously extracted from the ammonium sulfate solution formed in this system. The product stream from said neutralization step is sent to a phase separator where the solvent-lactam phase is separated from the ammonium sulfate solution phase. The ammonium sulfate phase is extracted with fresh solvent to remove residual amounts of lactam. The ammonium sulfate solution is then steam stripped to remove solvent and sent to an ammonium sulfate recovery unit. The solvent-lactam phase passes to a distillation tower where solvent is stripped from the lactam and the lactam is sent to storage.

Desirably, the crude lactam is further purified, e.g., in accordance with the purification process of U.S. Pat. No. 3,021,326, issued Feb. 13, 1962, to Snider et al. As discussed in this patent a very high purity caprolactam is required to assure good quality in polyamides produced therefrom. A troublesome problem has been to separate certain oxidizable organic impurities from the caprolactam. Presence of these impurities is indicated by reaction of the lactam with potassium permanganate solution. Quantitatively, the concentration of oxidizable impurities can be expressed as "permanganate number," P.N., found by adding 1 ml. of N/100 $KMnO_4$ aqueous solution to 50 ml. of 0.1% caprolactam aqueous solution; maintaining agitation for 250 seconds; and measuring optical density of the resulting mixture in a cell of 5 cm. path with light of 410 millimicron wavelength. This test shows the extent of oxidation of impurities by permanganate by measuring the intensity of yellow coloration due to oxidation product formed. P.N. values in this application are calculated by multiplying the measured optical density by 100, "optical density" being defined as $\log_{10}$ (light transmitted by the solvent/light transmitted by the solution). Surprisingly, I have found that at optimum conditions a crude lactam having P.N. of only about 310 is produced using a 1.14 acid/lactam ratio in the last stage of the two stage rearrangement system of the present invention. Crude lactam having such P.N. values is easily purified by known procedures, such as the process of U.S. Pat. No. 3,021,326, to produce preferred lactam products having P.N. of 2 or less.

The following examples are specific embodiments of my process, illustrating my invention and the best mode contemplated by me of carrying it out. Parts and percentages are by weight unless otherwise indicated.

EXAMPLE 1

About 72.5 parts per hour of cyclohexanone oxime containing 4.9 percent water was continuously fed to a first catalytic rearrangement zone containing a circulating reaction mass having a sulfuric acid to caprolactam weight ratio of 1.45 and a free $SO_3$ content of 5.9 percent. Equipment consisted of an in-line mixing unit connected in series with a flow meter, a heat exchanger and a circulation pump, arranged for circulating the reaction mass at a rate 40 times the feed of cyclohexanone oxime. The equipment was sized to provide a reaction time of about 0.5–5 hours. The oxime was pumped to the in-line mixer in the circulating reaction mass. All equipment and piping in contact with the reaction mass was 316 stainless steel. The temperature of the circulating reaction mass exit the heat exchanger was maintained at 80° C. and the peak temperature in the reaction mass was about 102° C. The sulfuric acid to caprolactam weight ratio of 1.45 in the circulating reaction mass was maintained by continuously adding oleum containing 25 weight percent $SO_3$ to the reaction mass. Exit the heat exchanger, a portion of the reaction mass equivalent to the feed thereto was continuously removed and fed to a second catalytic reaction zone having a sulfuric acid to caprolactam weight ratio of 1.14 and a free $SO_3$ content of about 3.2 percent. Equipment in the second catalytic rearrangement zone was similar to that used in the first catalytic rearrangement zone. About 19.6 parts per hour of cyclohexanone oxime containing 4.9 percent water was continuously pumped to the in-line mixer in the circulating reaction mass, which was circulated at a rate 32 times the rate of feeding said portion of the reaction mass from the first catalytic rearrangement zone. The temperature of the circulating reaction mass exit the heat exchanger was 80° C. and the peak temperature in the reaction mass was 86° C. Exit the heat exchanger, a portion of the reaction mass equivalent to the feed thereto was continuously withdrawn. The recovery of caprolactam from the portion of the circulating reaction mass withdrawn from the second catalytic rearrangement zone was accomplished by known processes in the manner described hereinabove. The crude lactam recovered had a P.N. of about 310. Yield of purified lactam was 99.1 percent calculated on the cyclohexanone oxime entered.

EXAMPLE 2

The procedure of Example 1 was followed except that a conventional static mixer was used in the first catalytic rearrangement zone instead of the in-line mixer of Example 1. It was found that the maximum free $SO_3$ that could be tolerated using the static mixer was about 4 weight percent $SO_3$, because the P.N. values increased very rapidly at higher free $SO_3$ concentrations. Surprisingly, an increase in free $SO_3$ to 10–12 weight percent or more showed relatively little effect when the in-line mixer was used to provide a relatively high degree of mixing intensity in the first catalytic rearrangement zone. Other means for providing vigorous mixing at the point of oxime addition gave similar results.

EXAMPLE 3

The procedure of Example 1 was followed except that the peak temperature in the first catalytic rearrangement zone was varied over the range 78°–105°C. The P.N.-peak temperature relationship was linear over the 78°–105° C. temperature range with significantly lower P.N. values at the lower temperatures.

EXAMPLE 4

The procedure of Example 1 was followed except that the reaction mass in the first catalytic rearrangement zone was circulated at a rate 266 times the feed of cyclohexanone oxime to said zone. Results indicated that the increased circulation rate gave no significant improvement in P.N. values or yield of product. However, a circulation rate at least 20 times the feed of oxime is desirable for adequate cooling of the reaction mixture in the heat exchanger.

EXAMPLE 5

The procedure of Example 1 was followed except that samples of the circulating reaction mass in the second catalytic rearrangement zone were taken at various points in the circulating stream corresponding to various reaction times following addition of the oxime. It was determined that the percent oxime in the reaction mass was reduced to 0.08 percent within 11.4 seconds after addition of the oxime. Oxime in the product stream was 0.07 percent.

I claim:

1. A process for the production of monocyclic lactams having 5 to 12 ring carbon atoms and one ring nitrogen atom by the catalytic rearrangement of a cycloalkanone oxime having 5 to 12 carbon atoms in the ring in the presence of oleum, comprising:

(a) continuously feeding a first portion of said cycloalkanone oxime consisting of 65 to 85 parts by weight of said cycloalkanone oxime having a water content of up to 6 weight percent to a first catalytic rearrangement zone containing a circulating reaction mass having a sulfuric acid to lactam weight ratio of 1.37 to 1.80, said lactam being the lactam corresponding to the cycloalkanone oxime being employed, a free $SO_3$ content of 2.4 to 14.0 weight percent, and a temperature of 50° to 105° C., said reaction mass being circulated at a rate at least 20 times the rate of feeding said cycloalkanone oxime to said first catalytic rearrangement zone;

(b) continuously feeding oleum to said first catalytic reaction zone in amount sufficient to maintain a sulfuric acid to lactam weight ratio of 1.37 to 1.80 in said zone, said oleum containing $SO_3$ in amount sufficient to react with all of the water in said cycloalkanone oxime and maintain the free $SO_3$ content of the circulating reaction mass at 2.4 to 14.0 weight percent;
(c) continuously feeding a portion of the circulating reaction mass from the first catalytic rearrangeent zone substantially equivalent to the feed of cycloalkanone oxime to said zone, to a second catalytic rearrangement zone containing a circulating reaction mass having a sulfuric acid to lactam weight ratio of at least 1.14, a free $SO_3$ content of at least 0.82 weight percent, and a temperature of 70° to 100° C., said reaction mass in said second catalytic rearrangement zone being circulated at a rate of at least 20 times the rate of feeding to said second catalytic rearrangement zone said portion of the circulating reaction mass from said first catalytic rearrangement zone;
(d) continuously feeding a second portion of said cycloalkanone oxime consisting of 15 to 35 parts by weight of said cycloalkanone oxime having a water content of up to 6 weight percent to said second catalytic rearrangement zone;
(e) continuously withdrawing a portion of the circulating reaction mass from the second catalytic rearrangement zone substantially equivalent to the feed to said zone; and
(f) recovering lactam from the portion of the circulating reaction mass withdrawn from the second catalytic rearrangement zone.

2. The process of claim 1 wherein the said cycloalkanone oxime is selected from the group consisting of cyclopentanone oxime, cyclohexanone oxime and methyl cyclohexanone oxime.

3. The process of claim 1 wherein the said cycloalkanone oxime is cyclohexanone oxime.

4. The process of claim 1 wherein the residence time of the said cycloalkanone oxime in contact with the oleum catalyst is at least 3–10 seconds at 70° to 100° C.

5. The process of claim 1 wherein the circulating reaction mass in the first catalytic reaction zone has a sulfuric acid to lactam weight ratio of 1.40 to 1.75, a free $SO_3$ content of 3.0 to 10.0 weight percent, and a temperature of 70° to 105° C. and oleum is added in step (b) to maintain said sulfuric acid to lactam weight ratio of 1.40 to 1.75 and said free $SO_3$ content of 3.0 to 10.0 weight percent.

6. The process of claim 1 wherein the circulating reaction mass in the second catalytic reaction zone has a sulfuric acid to lactam weight ratio of 1.14 to 1.31, and a free $SO_3$ content of 0.82 to 6.5 weight percent.

7. The process of claim 1 wherein the said cycloalkanone oxime is added to each of the two catalytic rearrangement zones with vigorous agitation.

8. A process for the production of caprolactam by catalytic rearrangement of cyclohexanone oxime in the presence of oleum comprising:
(a) continuously feeding a first portion of cyclohexanone oxime consisting of 65 to 85 parts by weight of cyclohexanone oxime having a water content of 0.1 to 5 weight percent to a first catalytic rearrangement zone containing a circulating reaction mass having a sulfuric acid to caprolactam weight ratio of 1.40 to 1.75, a free $SO_3$ content of 3.0 to 10.0 weight percent, and a temperature of 70° to 105° C., said reaction mass being circulated at a rate of 30 to 50 times the rate of feeding said cyclohexanone oxime to said first catalytic rearrangement zone;
(b) continuously feeding oleum to said first catalytic reaction zone in amount sufficient to maintain a sulfuric acid to caprolactam weight ratio of 1.40 to 1.75 in said zone, said oleum containing $SO_3$ in amount sufficient to react with all of the water in the cyclohexanone oxime and maintain the free $SO_3$ content of the circulating reaction mass at 3.0 to 10.0 weight percent;
(c) continuously feeding a portion of the circulating reaction mass from the first catalytic rearrangement zone substantially equivalent to the feed of cyclohexanone oxime to said zone, to a second catalytic rearrangement zone containing a circulating reaction mass having a sulfuric acid to caprolactam weight ratio of 1.14 to 1.31, a free $SO_3$ content of 0.82 to 6.5 weight percent, and a temperature of 70° to 100° C., said reaction mass in said second catalytic rearrangement zone being circulated at a rate 30 to 50 times the rate of feeding to said second catalytic rearrangement zone said portion of the circulating reaction mass from said first catalytic rearrangement zone;
(d) continuously feeding a second portion of the cyclohexanone oxime consisting of 15 to 35 parts by weight of the cyclohexanone oxime having a water content of 0.1 to 5 weight percent to said second catalytic rearrangement zone;
(e) continuously withdrawing a portion of the circulating reaction mass from the second catalytic rearrangement zone substantially equivalent to the feed to said zone; and
(f) recovering caprolactam from the portion of the circulating reaction mass withdrawn from the second catalytic rearrangement zone.

9. The process of claim 8 wherein the residence time of the cyclohexanone oxime in contact with the oleum catalyst is at least 3–10 seconds and the cyclohexanone oxime is added to each of the two catalytic rearrangement zones with vigorous agitation.

* * * * *